(12) United States Patent
Diao et al.

(10) Patent No.: US 11,493,692 B2
(45) Date of Patent: Nov. 8, 2022

(54) MULTI-SPOT LASER PROBE WITH MULTIPLE SINGLE-CORE FIBERS

(71) Applicant: Alcon Inc., Fribourg (CH)

(72) Inventors: Chenguang Diao, Irvine, CA (US); Mark Harrison Farley, Laguna Hills, CA (US); Alireza Mirsepassi, Irvine, CA (US); Ronald T. Smith, Irvine, CA (US); Timothy C. Ryan, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 17 days.

(21) Appl. No.: 17/172,342

(22) Filed: Feb. 10, 2021

(65) Prior Publication Data

US 2021/0255388 A1    Aug. 19, 2021

Related U.S. Application Data

(60) Provisional application No. 62/977,803, filed on Feb. 18, 2020.

(51) Int. Cl.
*A61B 18/22* (2006.01)
*A61B 18/00* (2006.01)
*G02B 6/26* (2006.01)

(52) U.S. Cl.
CPC .............. *G02B 6/262* (2013.01); *A61B 18/22* (2013.01); *A61B 2018/00172* (2013.01); *A61B 2018/2211* (2013.01); *A61B 2018/2244* (2013.01); *A61B 2018/2266* (2013.01)

(58) Field of Classification Search
CPC ................ A61B 2018/2211; A61B 2018/2244
See application file for complete search history.

(56) References Cited

U.S. PATENT DOCUMENTS

| | | | |
|---|---|---|---|
| 6,066,128 A | 5/2000 | Bahmanyar et al. | |
| 7,189,226 B2 | 3/2007 | Auld et al. | |
| 7,566,173 B2 | 7/2009 | Auld et al. | |
| 7,909,816 B2 | 3/2011 | Buzawa | |
| 8,398,240 B2 | 3/2013 | Smith | |
| 8,951,244 B2 | 2/2015 | Smith | |
| 9,055,885 B2 | 6/2015 | Horvath | |
| 10,245,181 B2 | 4/2019 | Diao | |
| 10,639,198 B2 | 5/2020 | Farley | |
| 11,213,426 B2 * | 1/2022 | Cook | G02B 6/032 |
| 11,259,960 B2 * | 3/2022 | Charles | A61B 90/92 |
| 11,291,470 B2 * | 4/2022 | Cook | A61B 18/20 |
| 2001/0012429 A1 | 8/2001 | Wach | |

(Continued)

*Primary Examiner* — Rhonda S Peace (57) ABSTRACT

The present disclosure relates to a laser probe assembly coupled to a laser system through an optical fiber cable. In one example, the laser probe assembly comprises a probe tip coupled to the probe body, the probe tip housing multiple fibers. Each of the multiple fibers comprises a proximal end that couples to the laser system and a distal end that terminates in the probe tip, a single core for transporting a laser beam provided by the laser system, and a cladding surrounding the core. The laser probe assembly also comprises a lens for projecting multiple laser beams provided by the multiple fibers on to a surgical site. Within the probe tip, parts of outer surfaces of portions of any two adjacent fibers of the multiple fibers touch. Also, the multiple fibers are at least substantially centered with respect to the lens.

15 Claims, 4 Drawing Sheets

(56) References Cited

U.S. PATENT DOCUMENTS

| | | |
|---|---|---|
| 2002/0045811 A1 | 4/2002 | Kittrell |
| 2004/0073120 A1* | 4/2004 | Motz .................... A61B 5/0084 |
| | | 600/478 |
| 2012/0191078 A1 | 7/2012 | Yadlowsky |
| 2013/0150839 A1 | 6/2013 | Smith |
| 2018/0055596 A1 | 3/2018 | Johnson |
| 2018/0243137 A1* | 8/2018 | Diao .................... G02B 6/3624 |
| 2018/0333304 A1* | 11/2018 | Diao .................... A61F 9/00823 |
| 2019/0117309 A1* | 4/2019 | Shelton ................. A61B 18/26 |
| 2019/0142544 A1 | 5/2019 | Horn |
| 2019/0175405 A1 | 6/2019 | Diao |
| 2020/0375660 A1 | 12/2020 | Lassalas et al. |
| 2020/0390598 A1* | 12/2020 | Charles .................. A61F 9/008 |
| 2020/0397614 A1* | 12/2020 | Diao ....................... G02B 6/06 |
| 2021/0255388 A1* | 8/2021 | Diao ..................... A61B 18/22 |

* cited by examiner

MULTI-SPOT LASER PROBE WITH MULTIPLE SINGLE-CORE FIBERS

PRIORITY CLAIM

This application claims the benefit of priority of U.S. Provisional Patent Application Ser. No. 62/977,803 titled "MULTI-SPOT LASER PROBE WITH MULTIPLE SINGLE-CORE FIBERS," filed on Feb. 18, 2020, whose inventors are Chenguang Diao, Mark Harrison Farley, Alireza Mirsepassi, Timothy C. Ryan and Ronald T. Smith, which is hereby incorporated by reference in its entirety as though fully and completely set forth herein.

FIELD

Embodiments of the disclosure relate to an apparatus and, more specifically, to a multi-spot laser probe with multiple single-core fibers.

BACKGROUND

In a wide variety of medical procedures, laser light is used to assist the procedure and treat patient anatomy. For example, in laser photocoagulation performed during retinal detachment surgery, a laser probe is used to cauterize blood vessels at laser burn spots across the retina. Certain types of laser probes burn multiple spots at a time, which may result in faster and more efficient photocoagulation. For example, a laser probe may be coupled, through an optical fiber cable, to a surgical laser system that splits a single laser beam into multiple laser beams that exhibit a laser spot pattern and delivers the laser beams to an array of individual optical fibers ("fibers") in the optical fiber cable that exhibit a corresponding fiber pattern. At their distal ends, the fibers are coupled to the laser probe and project the laser beam spots with the laser spot pattern onto the retina. Typically, the fibers should be tightly packed together so that the fiber pattern matches the laser spot pattern. Also, in part of a tip of the laser probe, a micro spacer may be used to provide the desired spacing between the laser burn spots by holding the fibers in a fixed geometrical relationship, thereby creating the desired laser spot pattern.

However, the use of a micro spacer when assembling a laser probe, in certain cases, may lead to a time consuming and difficult laser probe manufacturing process. This is because, in such an assembly process, each of the fibers is inserted into a separate corresponding opening or hole in the micro spacer. The fibers may further be bonded to the micro spacer by using an adhesive, which may result in a thermal robustness issue at a high laser power level.

In certain cases, instead of utilizing multiple individual fibers, a multi-core optical fiber (MCF) may be used. To create a MCF, first, holes are typically drilled into a rod, such as a fused silica rod, which may function or be referred to as an outer cladding. Then fused silica cores, that are used to transport laser beams, are consolidated within the drilled holes. In certain cases, dopants, such as fluorine or germanium, are also added to the outer surface of the cores. Dopants are added to create the required refractive index profile to support light guiding properties of the MCF. Finally, the fused silica rod is drawn at an elevated temperature to a desired diameter and length, resulting in the MCF. In an MCF, the holes are drilled with a certain spacing in between the hole in order to create the desired spacing between the laser burn spots. Further, the cores are tightly held together by the outer cladding, ensuring that the laser beams are propagated with the desired laser spot pattern.

However, manufacturing MCFs, in certain cases, does not provide the desired yield. For example, the dopants in an MCF may, in some cases, diffuse from, for example, the cores to the outer cladding. Such a diffusion may materially change the optical properties of the components of the MCF. In addition, dopant gradients can cause dopant diffusion, such that under high temperature gas bubbles may form in the making of MCFs towards interfaces between the cores and the outer cladding. The gas bubbles may reduce the yield of MCFs and weaken the MCF, leading to fragile fibers.

SUMMARY

According to one embodiment, the present disclosure is directed to a laser probe assembly coupled to a laser system through an optical fiber cable. In certain embodiments, the laser probe assembly comprises a probe tip coupled to the probe body, the probe tip housing multiple fibers. Each of the multiple fibers comprises a proximal end that couples to the laser system and a distal end that terminates in the probe tip, a single core for transporting a laser beam provided by the laser system, and a cladding surrounding the core. The laser probe assembly also comprises a lens for projecting multiple laser beams provided by the multiple fibers onto a surgical site. Within the probe tip, parts of outer surfaces of portions of any two adjacent fibers of the multiple fibers touch. Also, the multiple fibers are at least substantially centered with respect to the lens.

BRIEF DESCRIPTION OF THE DRAWINGS

For a more complete understanding of the present technology, its features, and its advantages, reference is made to the following description, taken in conjunction with the accompanying drawings, in which.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described example is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation can be combined with the features, components, and/or steps described with respect to other implementations of the present disclosure.

In certain embodiments, the term "about" refers to a +/−10% variation from the nominal value. It is to be understood that such a variation can be included in any value provided herein. Also, as used herein, the term "proximal" refers to a location with respect to a device or a portion of the device that, during normal use, is closest to the user using the device and farthest from the patient in connection with whom the device is used. Conversely, the term "distal" refers to a location with respect to the device or the portion of the device that, during normal use, is farthest from the user using the device and closest to the patient in connection with whom the device is used. For example, the terms "distal" and "proximal" as used herein may refer to a relative location with respect to an illumination system, optic fiber, microscope, or a portion thereof.

Embodiments provided herein generally relate to a system comprising a surgical laser system coupled to a laser probe through an optical fiber cable, which includes multiple single-core fibers whose proximal ends terminate at the surgical laser system and distal ends terminate in a probe tip of the laser probe. Portions of the multiple fibers within the probe tip are tightly held together and centered or at least substantially centered with respect to a lens that is placed within the probe tip. The multiple fibers comprise cores, claddings, and coatings, although the coatings may be striped from portions of the fibers in some cases. The diameters and thicknesses of these components are selected such that the desired spacing between the cores of the multiple fibers is achieved. Note that, herein, the term substantially refers to a range of approximately 0-5 microns. For example, the multiple fibers being at least substantially centered with respect to a lens refers to the multiple fibers being centered with respect to the lens with a range of approximately 0-5 microns.

Figure 1:
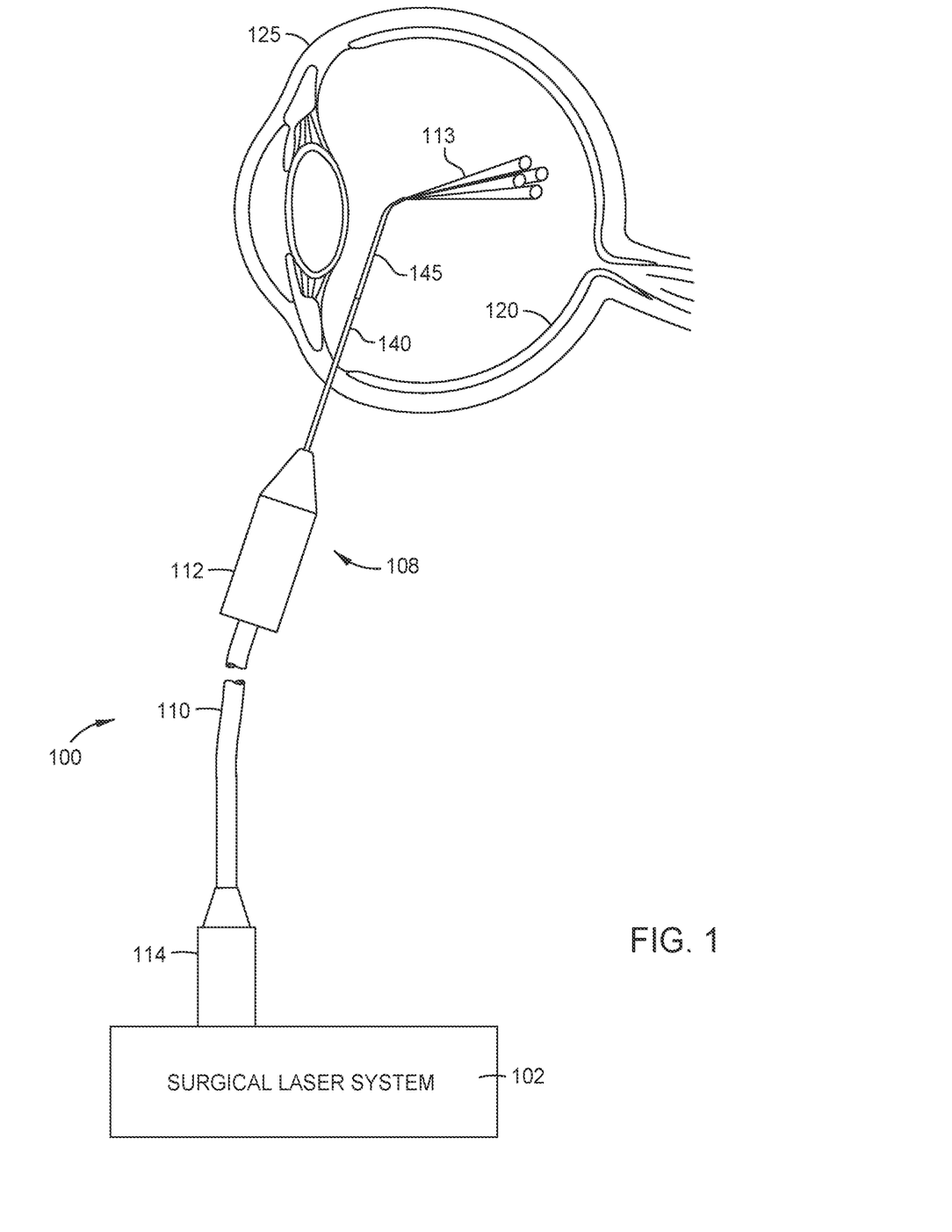
FIG. 1 illustrates a plan view of a system for generating laser beams for delivery to a surgical target, in accordance with a particular embodiment of the present disclosure.

FIG. 1 illustrates a plan view of a system 100 for generating laser beams for delivery to a surgical target, in accordance with a particular embodiment of the present disclosure. As shown, system 100 includes a surgical laser system 102 and a multi-spot probe ("probe") 108. The system 100 produces laser beams 113 with a laser spot pattern to be delivered to the retina 120 of a patient's eye 125, in one example. Probe 108 includes a probe body 112, a probe support sleeve 140, and a probe tip 145 (also referred to as a tube). Surgical laser system 102 and probe 108 are coupled together through an optical fiber cable 110. At its proximal end, optical fiber cable 110 couples to a port of surgical laser system 102 through a connector 114. Surgical laser system 102 is configured to deliver the laser beams 113 from the port to the probe 108 via multiple fibers contained in the optical fiber cable 110.

More specifically, the surgical laser system 102 includes a number of laser light sources (e.g., one or more laser light sources) for generating laser beams that can be used during an ophthalmic procedure. The surgical laser system 102 may be an ophthalmic surgical laser system configured to generate laser beams, also referred to as surgical treatment beams, to treat patient anatomy, e.g., perform photocoagulation. A user, such as a surgeon or surgical staff member, can control the surgical laser system 102 (e.g., via a foot switch, voice commands, etc.) to fire the laser beams.

In one example, in operation, a laser light source of surgical laser system 102 generates a laser beam that is split into multiple laser beams that exhibit a laser spot pattern. The multiple laser beams are then focused by a lens (e.g., a focusing lens) of surgical laser system 102 onto an interface plane (also referred to as a proximal entrance plane) of the exposed proximal ends of the fibers within the optical fiber cable 110. The multiple laser beams are focused such that each of the multiple laser beams is focused on the proximal end of a core of a different fiber contained in the optical fiber cable 110. The interface plane of the proximal ends of the fibers is exposed by a ferrule inserted into connector 114 through which optical fiber cable 110 connects to the surgical laser system 102. The multiple laser beams are transported through the entire lengths of the fibers to the probe 108, which is disposed at the distal end of the optical fiber cable 110. The multiple laser beams exit the probe tip 145, as laser beams 113, with the same laser spot pattern, and are projected onto the retina 120.

Figure 2:
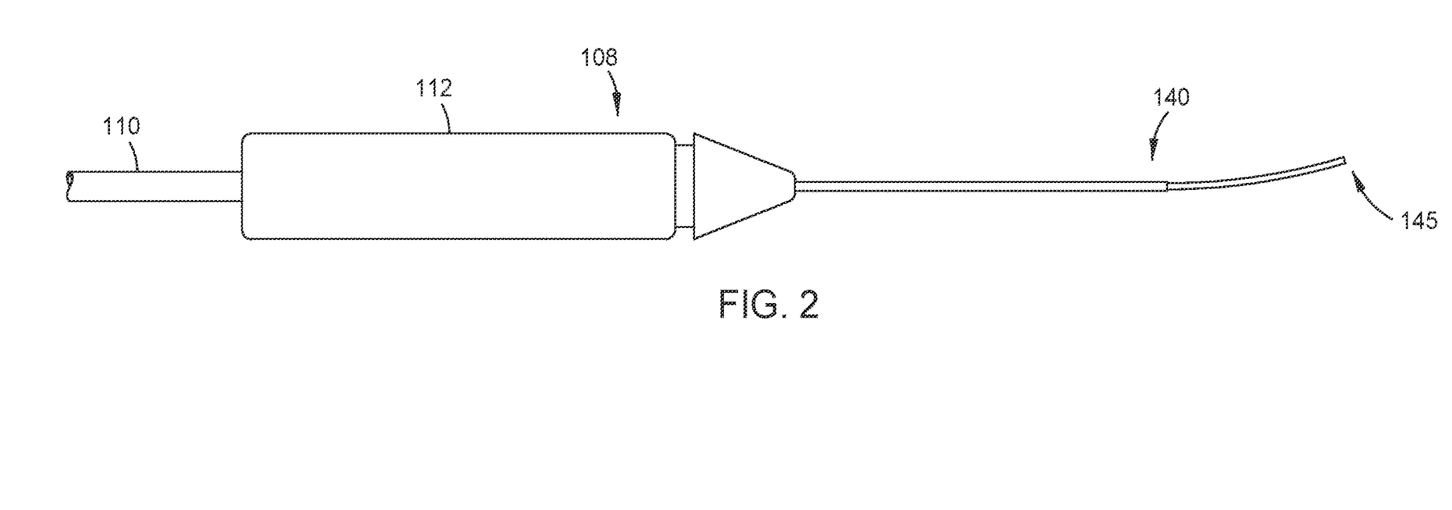
FIG. 2 illustrates a plan view of a probe, in accordance with a particular embodiment of the present disclosure.

FIG. 2 illustrates a plan view of the probe 108, in accordance with a particular embodiment of the present disclosure. As described above, the probe 108 includes a probe body 112 shaped and sized for grasping by a user. Extending from probe body 112 is support sleeve 140, which encompasses probe tip 145 that also extends from the probe body 112 and beyond the support sleeve 140. The support sleeve 140, in one example, is a stainless steel sleeve, although other similar materials are also within the scope of this disclosure. Probe tip 145, in one example, is made of an alloy, such as Nitinol, although other similar materials are also within the scope of this disclosure. The optical fiber cable 110 typically comprises multiple fibers surrounded by a polyvinyl chloride (PVC) tube for protecting fibers during handling. The fibers extend through the probe body 112 and into the probe tip 145. The laser beams 113 emanate from the distal ends of the fibers and, thereby, the distal end of the probe tip 145 onto the retina 120.

As described above, in certain cases, a micro spacer may be used in part of the probe tip 145 to provide the desired spacing between the cores of the fibers, which helps to provide the desired laser spot pattern for the laser burn spots. The micro spacer works by holding the fibers in a fixed geometrical relationship, thereby creating the desired laser spot pattern. However, the use of a micro spacer when assembling a laser probe, in certain cases, may lead to a time consuming and difficult laser probe manufacturing process, as described above.

Although in the example of FIGS. 1 and 2, multiple fibers are used in the optical fiber cable 110 to transport the laser beams, as described above, in some other cases, an MCF may be used instead. In certain cases, dopants, such as fluorine or germanium, are added to the outer surface of the cores of the MCF. However, manufacturing MCFs, in certain cases, does not provide the desired yield, as described above.

Accordingly, the embodiments described herein relate to the use of multiple separate single-core fibers, portions of which within the probe tip are tightly held together and at least substantially centered with respect to a lens that is also placed within the probe tip. The multiple fibers comprise cores, claddings, and coatings. The diameters and thicknesses of these components are also selected such that the desired spacing between the cores of the multiple fibers is achieved, thereby enabling the probe to provide the laser burn spots with the desired laser spot pattern.

Figure 3:
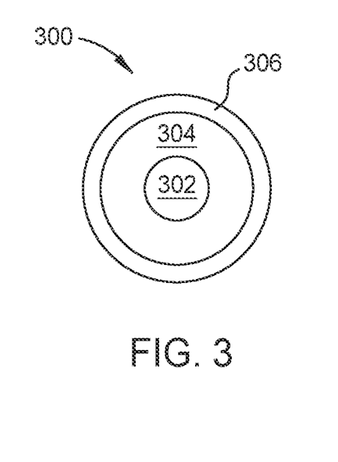
FIG. 3 illustrates an example front sectional view of a fiber including a core, cladding, and coating, in accordance with a particular embodiment of the present disclosure.

FIG. 3 illustrates an example front sectional view of a fiber 300 including a core 302, cladding 304, and coating 306, in accordance with a particular embodiment of the present disclosure. Core 302 may comprise any transparent material, such as fused silica or glass. Cladding 304 may also comprise transparent material, such as fused silica or glass. Coating 306, in one example, comprises polyimide or similar material.

In certain embodiments, core 302 is doped. For example, core 302 may be germanium-doped fused silica. Doping core 302 with germanium, or a similar dopant, helps with increasing the refractive index of core 302 compared to the refractive index of the fused silica of cladding 304 and hence creating light guiding properties within core 302.

In certain other embodiments, core 302 is not doped and instead cladding 304 is doped. For example, cladding 304, which comprises fused silica, is doped with a dopant that reduces the refractive index of cladding 304 relative to core 302. Example dopants may include fluorine (F), chlorine (Cl), or boron (B). Cladding 304, as doped, has a lower refractive index than the core 302, thereby creating light guiding properties within core 302.

In the example of FIG. 3, core 302 may have a diameter in the range of 50-100 μm (micrometer). In one example, core 302 has a 75 μm diameter, and therefore, a radius of 37.5 μm, measured from the center of the core 302. The cladding 304 and the core 302 together may have a diameter in the range of 100-15 μm. In the example where core 302 has a 75 μm diameter, the cladding 304 and the core 302 together may have a diameter of 125 μm, meaning that the thickness of cladding 304 may be 25 μm ((125 μm-75 μm)(2)/2). The cladding 304, the core 302, and the coating 306 together (i.e., fiber 300) may have a diameter in the range of 150-200 μm. In the example where core 302 has a 75 μm diameter and cladding 304 has a 25 μm thickness, the cladding 304, the core 302, and the coating 306 together may have a diameter of 175 μm, meaning that coating 306 may have a thickness of 25 μm ((175 μm-125 μm)/2). The dimensions provided here are only examples. Other diameters and thicknesses are within the scope of this disclosure.

Figure 4:
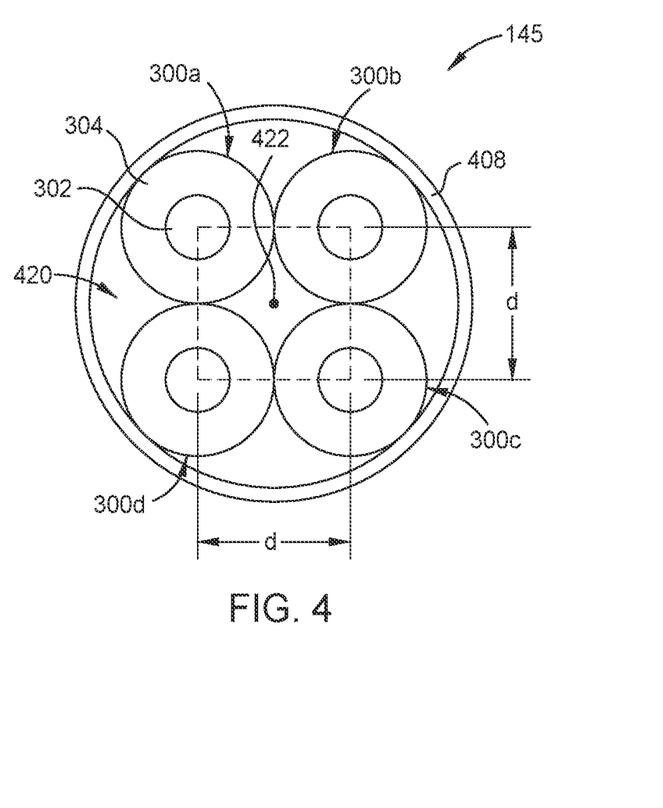
FIG. 4 illustrates an example front sectional view of portions of four fibers whose coatings have been stripped from such portions, in accordance with a particular embodiment of the present disclosure.

FIG. 4 illustrates an example front sectional view of portions of four fibers 300a-300d (collectively referred to as "fibers 300") whose coatings 306 have been stripped from such portions, in accordance with a particular embodiment of the present disclosure. More specifically, FIG. 4 shows a front sectional view of the portions of fibers 300 that are placed in a precision sleeve 408 within a probe tip (e.g., probe tip 145) of a probe (e.g., probe 108). A different view of precision sleeve 408 is provided in FIG. 5. Portions of fibers 300 whose coatings 306 have been stripped may be referred to as stripped portions. The coatings may not be stripped off of certain other portions of fibers 300, such as portions that are not placed in precision sleeve 408 or portions that extend through the optical fiber cable 110. Portions of fibers 300 whose coatings 306 have not been stripped may be referred to as non-stripped portions.

As shown, the cores 302 and claddings 304 of fibers 300 are sized such that fibers 300 are tightly held together in precision sleeve 408 and that the cores 302 of any two adjacent fibers have the same or at least substantially the same distance, d, from each other. Distance d refers to the core-to-core distance (e.g., distance between the centers of the cores) of adjacent fibers 300. Two adjacent fibers 300 are fibers that make contact with each other. For example, fiber 300a and 300b are adjacent with respect to each other but fiber 300a and 300c are not adjacent. Similarly, fibers 300b and 300c are adjacent but fibers 300b and 300d are not. In the example of FIG. 4, the diameter of a stripped portion of each fiber 300, is 125 μm, meaning that the radius is 62.5 μm. Accordingly, in the example of FIG. 4, the distance between the cores 302 of two adjacent fibers 300 is d=125 μm.

Precision sleeve 408 is a tubular dimensional shim that is configured to tightly hold fibers 300 together in order to maintain the desired distance between the cores 302 of fibers 300 and also to center fibers 300 with respect to a lens (e.g., cylindrical lens) placed in front of distal ends of fibers 300 (e.g., lens 514 of FIG. 5), as further described below. Fibers 300 being at least substantially centered with respect to the lens refers to center 422 of fibers 300 being aligned or at least substantially aligned with the center of lens 514, meaning the center 422 of fibers 300 and the center of lens 514 are along a same axis or at least substantially along the same axis. Further, the center of probe tip 145 is also along this same axis. Where there are four cores 302, center 422 corresponds to the intersection of the line segments that connect the centers of the cores 302 of non-adjacent fibers 300. The center 422 further corresponds to a point that is equidistant or at least substantially equidistant from the centers of the cores 302.

Precision sleeve 408 may comprise or be made of stainless steel, copper, polyimide, or any similar material. In certain cases, a precision sleeve is used because the inner diameter of probe tip 145 (e.g., a Nitinol tube) is larger than what is necessary to center fibers 300 with respect to the lens. For example, the probe tip 145 may have a standard size (e.g., 27 gauge) and be selected in order to accommodate the outer diameter of lens 514. As such, fibers 300 may be slightly loose in a standard size probe tip 145. The embodiments herein, therefore, provide precision sleeve 408 with the thickness and the dimensions required to ensure that fibers 300 are at least substantially centered with respect to the center of the lens, without the use of a micro spacer.

Selecting the right thickness and inner diameter for the precision sleeve 408 ensures that all the four fibers 300 are packed together and there is no room for any of the fibers 300 to be loose or move, thereby ensuring that desired distance between the cores 302 of fibers 300 are maintained, which in turn results in the desired laser spot pattern. For example, as shown, a part of the outer surface of cladding 304 of each fiber 300 touches the inner surface of the precision sleeve 408. Also, parts of the outer surface of cladding 304 of each fiber 300 touches parts of outer surfaces of claddings 304 of two adjacent fibers 300. Such an arrangement ensures that all fibers are confined from all sides and, therefore, not loose.

In the example where the distance between cores 302 of two adjacent fibers 300 is 125 μm, the inner diameter of precision sleeve 408 may be around 302 μm. But more generally, the inner diameter of precision sleeve 408 may be in the range of 302+/−25 µm. In certain aspects, adhesives are used to further hold the fibers 300 inside precision sleeve 408 in place. For example, an adhesive may fill all areas within the inner cylindrical space of the precision sleeve 408 that are not occupied by fibers 300. FIG. 4 illustrate areas 420 that are not occupied by fibers 300 and may be filled with adhesives. Example adhesives that may be used include a 2-part epoxy, such as HYB-353ND or similar material.

Although in the example of FIG. 4 four fibers 300 are packed within precision sleeve 408, in other embodiments, a smaller or a larger number of fibers 300 are used. Also, in certain embodiments, a fiber, such as an illumination fiber may extend in the middle of fibers 300. In such an example, the proximal end of the illumination fiber terminates at the surgical laser system 102, which propagates an illumination light onto an interface plane of the illumination fiber for illuminating the ocular space.

Figure 5:
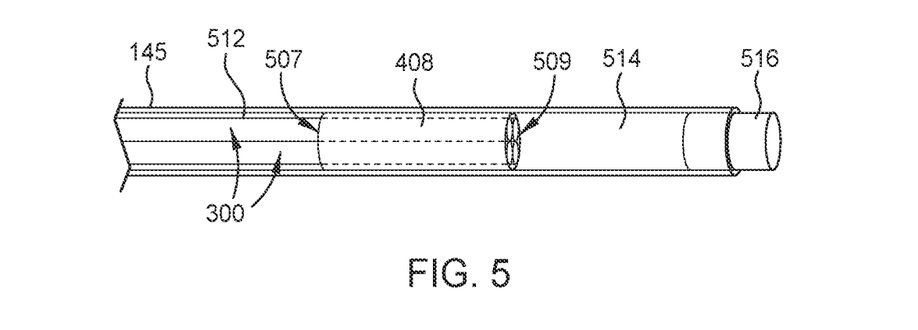
FIG. 5 illustrates an example perspective view of a distal end of a probe tip, in accordance with a particular embodiment of the present disclosure.

FIG. 5 illustrates an example perspective view of a distal end of probe tip 145, in accordance with a particular embodiment of the present disclosure. As shown, a protective component 516 (e.g., also referred to as a window) is placed at the distal opening of probe tip 145. Protective component 516 may be press-fitted into the distal opening in order to protect lens 514 by restricting movements of lens 514 along probe tip 145 and/or also by preventing lens 514 from detaching from probe tip 145. Lens 514 (e.g., gradient index (GRIN) lens) projects and focuses the laser beams that are propagated by fibers 300 inside precision sleeve 408. As shown, precision sleeve 408 comprises a distal opening 509 as well as a proximal opening 507. Fibers 300 extend beyond a proximal sleeve 512, which wraps around fibers 300, and into the proximal opening 507 of precision sleeve 408. Proximal sleeve 512 may be made of polyimide. Coatings 306 of fibers 300 may also be stripped from portions of fibers 300 that are wrapped around by proximal sleeve 512. Note that although lens 514 is a cylindrical lens, one of ordinary skill in the art appreciates that one of a variety of other types of lenses may be used instead.

Fibers 300 further extend along the length of precision sleeve 408 such that, in some examples, the distal ends of fibers 300 terminate where the distal end of precision sleeve 408 terminates (e.g., distal ends of fibers 300 are flush with the distal end of precision sleeve 408) and, in other examples, the distal ends of fibers 300 may extend beyond the distal end of precision sleeve 408 by a small amount. As such, fibers 300 propagate laser beams through the distal opening 509 of precision sleeve 408 and into lens 514. Note that FIG. 5, shows the stripped portions of fibers 300 where the coatings 306 have been stripped off of fibers 300. In certain embodiments, the outer diameter of precision sleeve 408 is aligned or at least substantially aligned with and the same or substantially the same as the outer diameter of lens 514. As described above, the diameter of the stripped portion of each of the fibers 300 (e.g., the diameter of the core 302 and cladding 304) is selected such when the four fibers 300 are tightly packed together in precision sleeve 408, the desired spacing between cores 302 of the fibers 300 is achieved, thereby producing the desired laser spot pattern, without the use of a micro spacer.

Figures 6, 7:
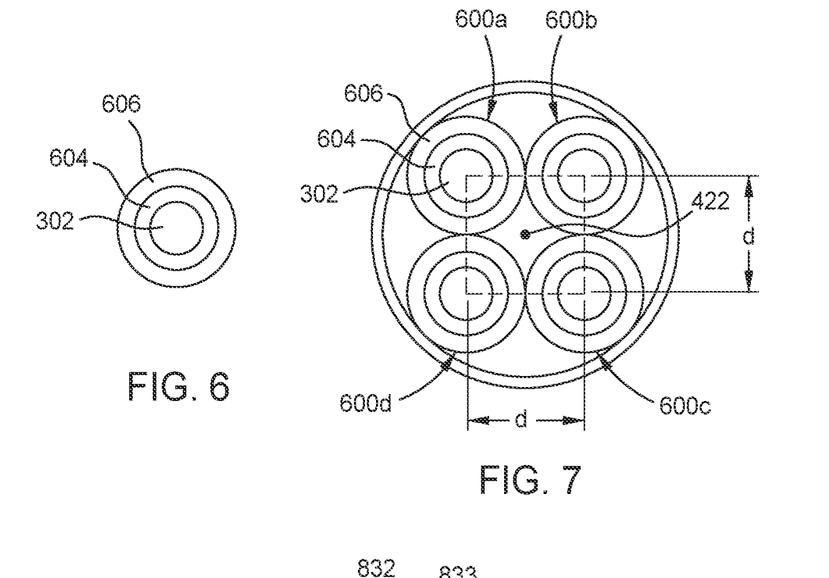
FIG. 6 illustrates an example fiber including a core, cladding, and coating, in accordance with a particular embodiment of the present disclosure.
FIG. 7 illustrates an example of four fibers, each including a core, cladding, and coating, in accordance with a particular embodiment of the present disclosure.

FIG. 6 illustrates an example fiber 600 including a core 302, cladding 604, and coating 606, in accordance with a particular embodiment of the present disclosure. Fiber 600 is similar to fiber 300 in all aspects, except for the thickness of cladding 604 and coating 606. In one example, the diameter of core 302 and cladding 604 together may be in the range of 60-120 µm. In the example where the diameter of core 302 is 75 µm, the diameter of core 302 and cladding 604 together may be 90 µm, meaning that the thickness of cladding 604 may be 15 µm. Also, the diameter of fiber 600, including core 302, cladding 604, and coating 606 may be in the range of 90-160 µm. In the example where the diameter of core 302 and cladding 604 together is 90 µm, the diameter of fiber 600 may be 125 µm, meaning that the thickness of coating 606 may be 35 µm. In the example of FIG. 6, fiber 600 has the same or at least substantially the same diameter as the stripped portion of fiber 300. Because fiber 600 has a smaller diameter than the non-stripped portion of fiber 300, four fibers 600 may be used in precision sleeve 408 without any portion of fibers 600 having to be stripped.

FIG. 7 illustrates an example of four fibers 600a-600d, each including a core 302, cladding 604, and coating 606, in accordance with a particular embodiment of the present disclosure. As shown, the distance, d, between the cores 302 of any two adjacent fibers 600 is the same or at least substantially the same. In the example of FIG. 7 where the outer diameter of each of the fibers 600 is 125 d is 125 µm. Also, similar to FIG. 4, the thickness of the precision sleeve 408 as well as the diameter of fibers 600 are selected such that the center 422 of fibers 600 is at least substantially aligned with the center of lens 514, meaning the center 422 of fibers 600 and the center of lens 514 are along a same axis. Further, the center of probe tip 145 is also along this same axis. Similar to FIG. 4, in FIG. 7, the outer diameter of precision sleeve 408 is at least substantially aligned with and at least substantially the same as the outer diameter of lens 514.

The diameters and thickness measurements provided with respect to FIGS. 3-6 are merely for illustration purposes. As discussed, any combination of diameters and thicknesses may be used as long as the center of the fibers inside a precision sleeve is at least substantially aligned with the front sectional center of lens 514 or the front sectional center of probe tip 145. The diameters and thicknesses of the various components described herein are also a function of the gauge size of the probe tip as well as the desired core-to-core distance d between the cores of any two adjacent fibers. Also, in certain embodiments, one or more of the diameters and thickness measurements described above may be +/−25 µm, or anywhere within that range, such as +/−5 or +/−3 µm.

Figure 8A:
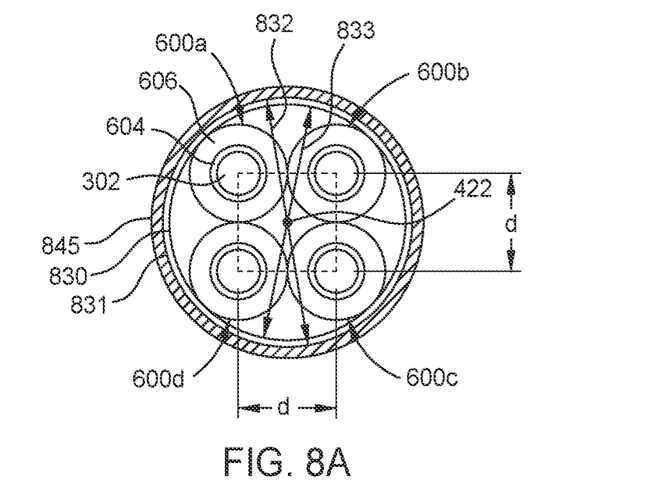
FIG. 8A illustrates a front sectional view of four fibers placed in a probe tip, in accordance with a particular embodiment of the present disclosure.

FIG. 8A illustrates a front sectional view of four fibers 600a-600d placed in a probe tip 845, in accordance with a particular embodiment of the present disclosure. In the example of FIG. 8A, fibers 600 are at least substantially centered with respect to lens 514 without the use of a precision sleeve or a micro spacer. As shown, probe tip 845 comprises a counter-bored portion 831 with an inner diameter of 832 as well as a non-counter-bored portion 830 with a larger inner diameter 833. A different view of probe tip 845 of the counter-bored portion 831 and non-counter-bored portion 830 are shown. In one example, inner diameter 832 may be between 305 µm-310 µm. Inner diameter 833 may be between 335 µm-345 µm.

Figure 8B:
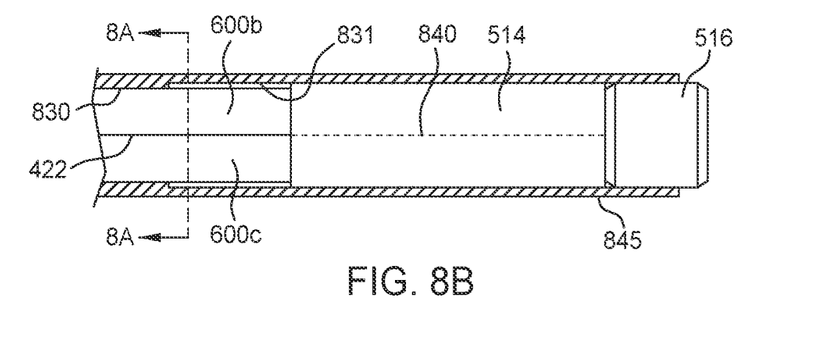
FIG. 8B illustrates a side view of fibers, a lens, and a protective element, all placed in probe a tip, which is shown cross-sectionally, in accordance with a particular embodiment of the present disclosure.

The non-counter-bored portion 830 tightly holds fibers 600 together and centers them with respect to lens 514, which, as shown in FIG. 8B, is placed in the counter-bored portion 831. As shown in FIG. 8A, the distance, d, between any two adjacent cores 302 of fibers 600 is at least substantially the same. In the example of FIG. 8A where the outer diameter of each of the fibers 600 is 125 µm, d is 125 µm.

FIG. 8B illustrates a side view of fibers 600, lens 514, and protective element 516, all placed in probe tip 145, which is shown cross-sectionally, in accordance with a particular embodiment of the present disclosure. As illustrated in FIG.

8B, the non-counter-bored portion 830 has at least substantially centered fibers 600 with respect to lens 514. More specifically, the center 422 of fibers 600 and the center of lens 514 are along a same axis.

Accordingly, the embodiments described herein allow for using multiple single-core fibers in a probe tip and centering the multiple single-core fibers with respect to a lens in the probe tip without the use of a micro spacer. The diameters and thicknesses of the components (e.g., core, cladding, and/or coating) of the fibers as well as the precision sleeve or the non-counter-bored segment of the probe tip are selected such that the desired spacing between the cores of the multiple fibers is achieved and the fibers are at least substantially centered with respect to the lens.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A laser probe assembly coupled to a laser system through an optical fiber cable, the laser probe comprising:
    a probe body;
    a probe tip coupled to the probe body, the probe tip housing multiple fibers, wherein each of the multiple fibers comprises:
        a proximal end that couples to the laser system and a distal end that terminates in the probe tip;
        a single core for transporting a laser beam provided by the laser system; and
        a cladding surrounding the core;
    a gradient index (GRIN) lens for projecting and focusing the multiple laser beams provided by the multiple fibers on to a surgical site, wherein:
        within the probe tip, parts of outer surfaces of portions of any two adjacent fibers of the multiple fibers touch;
        the multiple fibers are at least substantially centered with respect to the GRIN lens such that a center of the multiple fibers is at least substantially aligned with a center of the GRIN lens;
    wherein the multiple fibers are at least substantially centered with respect to the GRIN lens using a precision sleeve that surrounds the portions of the multiple fibers, and wherein an inner surface of the precision sleeve touches an outer surface of each of the portions of the multiple fibers; and wherein an outer diameter of the precision sleeve is at least substantially aligned with and at least substantially the same as an outer diameter of the GRIN lens;
    wherein the probe tip further has an inner diameter and wherein the precision sleeve is a tubular dimensional shim that fits inside the probe tip inner diameter;
    wherein the multiple fibers comprise second portions, the second portions of the multiple fibers comprise coatings around corresponding claddings of the multiple fibers;
    wherein the portions of the multiple fibers within the precision sleeve are without the coatings.

2. The laser probe assembly of claim 1, wherein the parts of the outer surfaces of the portions of any two adjacent fibers comprise parts of outer surfaces of claddings of the portions of the any two adjacent fibers.

3. The laser probe assembly of claim 2, wherein a first diameter of the core of each of the multiple fibers is in a range of 50-100 μm.

4. The laser probe assembly of claim 3, wherein a second diameter of the core and the cladding of each of the multiple fibers together is in a range of 100-150 μm.

5. The laser probe assembly of claim 1, wherein:
    the parts of the outer surfaces of the portions of any two adjacent fibers comprise parts of outer surfaces of coatings of the portions of any two adjacent fibers.

6. The laser probe assembly of claim 5, wherein a first diameter of the core of each of the multiple fibers is in a range of 50-100 μm.

7. The laser probe assembly of claim 6, wherein a second diameter of the core and the cladding of each of the multiple fibers together is in a range of 60-120 μm.

8. The laser probe assembly of claim 7, wherein a third diameter of the core, the cladding, and the coating of each of the multiple fibers together is in the range of 90-160 μm.

9. The laser probe assembly of claim 1, wherein:
    the probe tip comprises a counter-bored portion and a non-counter-bored portion, wherein an inner diameter of the counter-bored portion is larger than an inner diameter of the non-counter-bored portion; and
    the multiple fibers are confined by the non-counter-bored portion;
    the multiple fibers are at least substantially centered with respect to the lens by being confined in the non-counter-bored portion.

10. The laser probe assembly of claim 1, a distance between cores of the any two adjacent fibers is at least substantially the same.

11. The laser probe assembly of claim 1, wherein an adhesive is used in areas within an inner cylindrical space of the precision sleeve that is not occupied by the multiple fibers.

12. The laser probe assembly of claim I, wherein the precision sleeve is made of stainless steel and the probe tip is made of nitinol.

13. The laser probe assembly of claim 1, wherein the fiber distal ends terminate at a distal end of the precision sleeve.

14. The laser probe assembly of claim 13, wherein the fiber distal ends are flush with a distal end of the precision sleeve.

15. The laser probe assembly of claim 1, further comprising a support sleeve that encompasses the probe tip at a probe tip proximal end.

* * * * *